(12) United States Patent
Hamrock et al.

(10) Patent No.: US 6,780,472 B2
(45) Date of Patent: Aug. 24, 2004

(54) FLOOR FINISH COMPOSITIONS

(75) Inventors: Steven J. Hamrock, St. Paul, MN (US); Fidelis C. Onwumere, Mansfield, TX (US); Bradford B. Wright, Woodbury, MN (US); Michael A. Yandrasits, Hastings, MN (US)

(73) Assignee: 3M Innovative Properties Company, St. Paul, MN (US)

(*) Notice: Subject to any disclaimer, the term of this patent is extended or adjusted under 35 U.S.C. 154(b) by 98 days.

(21) Appl. No.: 10/027,933

(22) Filed: Dec. 19, 2001

(65) Prior Publication Data

US 2003/0087981 A1 May 8, 2003

Related U.S. Application Data

(62) Division of application No. 09/799,417, filed on Mar. 5, 2001, now abandoned, which is a continuation of application No. 09/242,078, filed as application No. PCT/US96/14666 on Sep. 13, 1996, now Pat. No. 6,197,844.

(30) Foreign Application Priority Data

Sep. 13, 1996 (WO) ................................ PCT/US96/14666

(51) Int. Cl.$^7$ .................................................. C08F 2/46
(52) U.S. Cl. ................ 427/402; 427/412.1; 427/412.4; 427/314; 427/316; 427/553; 427/541; 427/555; 427/558; 427/487; 427/508; 427/510; 427/512; 427/322; 427/299; 522/84; 522/86; 522/178; 522/173; 522/174; 522/182; 522/188; 501/201; 501/212; 501/206; 524/800; 524/804; 524/914
(58) Field of Search ................................ 427/487, 508, 427/510, 512, 532, 541, 553, 555, 558, 299, 314, 316, 322, 412.1, 412.4; 522/84, 86, 173, 178, 174, 182, 188; 524/800, 804, 914; 501/201, 216, 206

(56) References Cited

U.S. PATENT DOCUMENTS

| | | | |
|---|---|---|---|
| 3,845,056 A | | 10/1974 | Robson et al. |
| 3,949,107 A | * | 4/1976 | Schoenholz et al. ........ 427/316 |
| 4,111,878 A | * | 9/1978 | Ruhf .......................... 524/376 |
| 4,128,537 A | | 12/1978 | Markiewitz |
| 4,148,944 A | * | 4/1979 | Ruhf .......................... 427/256 |
| 4,195,146 A | | 3/1980 | Markiewitz et al. |
| 4,208,468 A | * | 6/1980 | Cunningham et al. ... 428/317.1 |
| 4,284,776 A | | 8/1981 | Gruber et al. |
| 4,420,499 A | * | 12/1983 | Bolgiano et al. ............ 427/520 |
| 4,485,226 A | | 11/1984 | Noll et al. |
| 4,491,663 A | | 1/1985 | Kordomenos et al. |
| 4,548,690 A | | 10/1985 | Peterson |
| 4,622,360 A | * | 11/1986 | Gomi et al. ................. 524/507 |
| 4,652,274 A | | 3/1987 | Boettcher et al. |
| 4,749,508 A | * | 6/1988 | Cockrell et al. ............ 510/201 |
| 4,812,489 A | | 3/1989 | Watanabe et al. |
| 4,855,334 A | | 8/1989 | Maruyama et al. |
| 4,869,934 A | * | 9/1989 | Jethwa ..................... 427/393.5 |
| 4,877,459 A | * | 10/1989 | Cockrell et al. .............. 134/40 |
| 4,902,440 A | | 2/1990 | Takeyama et al. |
| 5,191,002 A | * | 3/1993 | Davis ......................... 524/157 |
| 5,234,970 A | | 8/1993 | Kyle |
| 5,369,140 A | | 11/1994 | Valet et al. |
| 5,449,702 A | | 9/1995 | Tayama et al. |
| 5,464,680 A | * | 11/1995 | Hauser et al. .............. 428/141 |
| 5,494,707 A | * | 2/1996 | Wang et al. ............. 427/412.1 |
| 5,538,760 A | * | 7/1996 | Sharma .................... 427/388.4 |
| 5,548,018 A | * | 8/1996 | Maekawa .................... 524/517 |
| 5,637,599 A | * | 6/1997 | Levy et al. .................. 514/326 |
| 5,674,934 A | * | 10/1997 | Schmidt et al. ............. 524/555 |
| 5,700,768 A | * | 12/1997 | Lu ............................. 510/214 |
| 5,719,227 A | | 2/1998 | Rosenberry et al. |
| 5,837,422 A | | 11/1998 | Sasaki et al. |
| 5,843,576 A | | 12/1998 | Rosenberry et al. |
| 5,932,350 A | * | 8/1999 | Lauer et al. .............. 428/411.1 |
| 5,977,042 A | * | 11/1999 | Hernandez et al. ......... 510/201 |
| 6,096,383 A | | 8/2000 | Berg et al. .................. 427/493 |
| 6,361,826 B2 | * | 3/2002 | Olson et al. ................ 427/189 |

FOREIGN PATENT DOCUMENTS

| | | | |
|---|---|---|---|
| CA | 2159265 | 3/1996 | |
| EP | 0 549 116 A2 | 6/1993 | |
| JP | 3-7736 | 1/1991 | |
| JP | 3-39366 | 2/1991 | |
| JP | 4-171451 | 6/1992 | |
| WO | WO 01/14481 A1 | 3/2001 | ............ C09D/9/00 |
| WO | WO 0114481 A1 * | 3/2001 | |

OTHER PUBLICATIONS

Hawely's Condensed Chemical Dictionary, 13$^{th}$ ED, 1997, p 765.

* cited by examiner

Primary Examiner—James J. Seidleck
Assistant Examiner—Sanza L. McClendon
(74) Attorney, Agent, or Firm—Sean J. Edman

(57) ABSTRACT

A monomer useful in the formulation of a radiation curable coatable composition comprises (a) polyfunctional isocyanurate having at least three terminal reactive groups reacted with (b) hydroxyalkyl acrylate and (c) tertiary amine alcohol in a molar ratio of a:b:c of about 1:1–2.5:0.5–2, wherein b+c is at least 3 and no greater than the total number of terminal reactive groups of (a). The monomer is included in a radiation curable coatable composition suitable for use as a floor finish and in a floor finishing system comprising the foregoing coatable composition with a primer. A method for the treatment of a substrate using the floor finish and the floor finishing system is also described.

18 Claims, No Drawings

FLOOR FINISH COMPOSITIONS

This is a divisional of application Ser. No. 09/799,417 filed Mar. 5, 2001, which is a continuation of application Ser. No. 09/242,078, filed Feb. 4, 1999, (now U.S. Pat. No. 6,197,844), which was a national stage filing under 35 U.S.C. 371 of PCT/US96/14666, filed Sep. 13, 1996, which International Application was published in English by the International Bureau on Mar. 19, 1998.

The present invention relates to a radiation curable coatable composition suitable for use as a floor finish, to a floor finishing system utilizing the composition, to a method for applying a protective coating to a substrate, to substrates coated with the compositions and to a polyfunctional isocyanurate monomer useful in the formulation of the radiation curable coatable compositions.

BACKGROUND OF THE INVENTION

Polymer compositions are used in the formulation of various coating compositions such as floor finishes, for example. Commercially available floor finish compositions typically are aqueous emulsion based polymer compositions comprising one or more organic solvents, plasticizers, coating aids, antifoaming agents, polymer emulsions, waxes and the like. These compositions typically comprise a relatively low solids content (e.g., about 15–35%). The polymer composition is applied to a floor surface and then allowed to dry in air, normally at ambient temperature and humidity to form a film that serves as a protective barrier against soil deposited on the floor by pedestrian traffic, for example.

Although many of the commercially available floor finishes have performed well and have experienced at least some commercial success, the available finishes have been less than completely satisfactory for several reasons. For example, when applying conventional floor finish compositions to the surface of a floor, several coating applications are typically required to obtain a finish with a suitable appearance. Each successive-application of the composition must be dried before additional coatings are applied and/or before pedestrian traffic is allowed across the treated floor. The compositions are normally dried at ambient temperature and humidity in air, so that the drying time depends upon the air flow over the floor as well as the relative humidity of the air. Conventional floor finishes will soften when exposed to water for short periods or when exposed to strong chemical cleaners during a scrubbing operation, for example. Moreover, such finishes require almost daily maintenance (e.g., buffing) to provide a sustained and desirable appearance.

In light of the foregoing, it is desirable to provide a floor finish composition that can be applied in a single application and immediately dried and hardened in air to provide a durable, low maintenance, water-resistant, chemically resistant finish that does not require labor intensive (e.g., daily) maintenance to provide a sustained and desirable appearance. It would also be desirable to provide such a durable, low maintenance, water-resistant, chemically resistant finish in a form that can readily be removed from the surface to which it is applied, such as from flooring comprising conventional vinyl floor tiles, for example.

It is known that irradiation of ethylenically unsaturated compounds in the presence of a photoinitiator induces photopolymerization. As used herein, "photoinitiator" refers to any substance or combination of substances that interact with light to generate free radicals capable of inducing free radical polymerization. Photochemical or photoinitiated free radical polymerizations occur when radicals are produced by ultraviolet ("UV") and/or visible light irradiation of a free radical polymerizable reaction system. Energy absorption by one or more compounds in the system results in the formation of excited species, followed by either subsequent decomposition of the excited species into radicals or interaction of the excited species with a second compound to form radicals derived from both the initially excited compound and from the second compound. The exact mechanism for photoinitiation is not always clear and may involve either or both of the aforementioned pathways.

Photochemical polymerization has been applied in the formation of decorative and/or protective coatings and inks for metal, paper, wood and plastics as well as in photolithography for producing integrated and printed circuits and in curing dental materials. Many of the known applications involve a combination of photopolymerization and crosslinking with the crosslinking typically achieved by the used of ethylenically polyunsaturated monomers. Acrylate based systems are common as well as those based on unsaturated polyester and styrene.

Additionally, UV curable protective finishes have been applied to vinyl "no wax" flooring during the sheet manufacturing process to provide gloss as well as abrasion resistance. These protective finishes generally cannot be easily stripped from the flooring to which they are applied using conventional stripping methods (e.g., by the application of a chemical stripping composition with a stripping pad or brush). Furthermore, the curing of these finishes is typically carried out using high intensity light. The lamps have high power requirements, large power supplies and generally require ducted venting to remove ozone. Often, these finishes are cured in an inert atmosphere to overcome the deleterious effects of oxygen on the curing process. Because of the above noted power requirements and the like, the use of UV curable polymeric systems in the treatment of flooring has generally been limited to factory scale processes where the expense and additional burdens associated with these systems is more easily justified.

Other problems have been noted in the formulation of UV curable systems for pre-existing flooring (e.g., previously installed in a building). In the application of any type of finish to an existing floor, it is generally preferred that the hardened floor finish not alter the color of the floor. To accomplish this goal, the finish should be transparent and substantially free of observable color. This goal is especially desired in the maintenance of floors composed of white floor tiles where an observable color in the hardened finish will more noticeably produce an observable discoloration in the floor. Additionally, to make a floor finish composition acceptable for application in the field, the applied floor finish should also have low odor prior to curing.

It is known, for example, that certain resins containing functional polymerizable vinyl groups, such as acrylate or vinyl ether/maleate containing an amine or a thiol, are polymerizable in air by free radical polymerization when exposed to UV or visible light in the presence of a photoinitiator. Although tough, abrasion resistant coatings can be provided using such resins, the resulting coatings are typically colored, with colors ranging from yellow to dark orange or have an objectionable odor prior to curing. Consequently, these resins are considered unsuitable for use as floor finishes.

As mentioned, atmospheric oxygen is known to inhibit photoinitiated polymerization reactions, resulting in little or no cure on the surface of the coating or providing a coating with poor surface properties. Various processing techniques have been proposed to eliminate the effects of oxygen from the reacting resin. One approach is to isolate the coating in a chamber and purge the chamber with an inert gas (e.g., nitrogen) so that the polymerization reaction proceeds in an environment substantially free of oxygen. Another approach is to initiate the polymerization reaction using intense UV radiation in conjunction with the high levels of photoinitiator in the uncured resin. Neither of these proposed techniques are practical in providing a floor finish system for use on previously installed flooring. Although smaller, lightweight, inexpensive, low intensity light sources capable of operating on batteries or on 110 volt, 15 amp circuitry would be preferred, known UV curable polymer systems have experienced slower rates of cure and higher cure inhibition when low intensity light has been used.

A long felt and unsolved need exists for a coatable composition suitable for use as a floor finish that can easily be applied to a substrate, such as a previously installed floor, and hardened in air upon exposure to low intensity radiation such as ultraviolet light, for example. It is desirable to provide such a coatable composition, preferably without objectionable odor, in a form that may be easily applied to a floor and subsequently hardened to provide a protective coating substantially free of observable color. It is also desirable to provide the foregoing protective coatings in a form that allows them to be removed from the floor (e.g., by a suitable chemical stripper), as desired.

SUMMARY OF THE INVENTION

The invention provides a coatable composition that can be cured quickly in air by exposure to low intensity ultraviolet radiation to provide a durable protective coating for a suitable substrate such as vinyl floor tile, for example. The resulting coating requires little maintenance and can be easily and quickly stripped from the substrate by application of a suitable stripper composition, all as set forth herein.

In one aspect, the invention provides a monomer useful in the formulation of radiation curable coatable compositions, comprising (a) polyfunctional isocyanurate having at least three terminal reactive groups reacted with (b) hydroxyalkyl acrylate and (c) tertiary amine alcohol in a molar ratio of a:b:c of about 1:1–2.5:0.5–2, wherein b+c is at least 3 and no greater than the total number of terminal reactive groups of (a).

A preferred monomer comprises a compound having the general formula:

or $R_3$ and $R_4$ may together form a divalent cylcoalkanediyl, oxacycloalkanediyl, or azacycloalkanediyl bridging group having from 2 to 12 carbon atoms; and $Z_1$, $Z_2$, $Z_3$, $Z_4$, $Z_5$, and $Z_6$ independently represent divalent groups having from 1 to 18 carbon atoms, preferably alkanediyl groups (straight, branched or cyclic) having from 1 to 18 carbon atoms, most preferably, straight chain alkanediyl groups having from 1 to 4 carbon atoms.

The foregoing monomer is formulated into radiation curable coatable compositions as a first monomer by combining it with a second monomer and photoinitiator. The first monomer preferably comprises the reaction product of a trimer of hexane diisocyanate (optionally mixed with an allophanate of hexane diisocyanate), a hydroxyalkyl acrylate, and a tertiary amine alcohol. The first monomer is typically present within the composition in an amount between about 10 and 80 wt %. The second monomer can be selected from any of a variety of polymerizable monomers. Preferably, the second monomer is an acrylate, as is further described herein. The second monomer is typically present within the composition in an amount between about 5 and 90 wt %. In addition to the second monomer, the composition may further comprise additional polymerizable monomers, including combinations of two or more such monomers. A suitable photoinitiator is included within the composition to facilitate curing by UV radiation. Preferred are those initiators suitable in the formation of clear coatings having a low degree of observable color. Photoinitiator concentrations within the composition may vary depending on the nature of the other components of the composition and the nature of the photoinitiator. A typical concentration for the photoinitiator is between about 2 and 10% by weight.

Certain terms will be understood to have certain meanings, as set forth herein. "Ultraviolet radiation" and "UV radiation" are used interchangeably to refer to the spectrum of light comprising wavelengths within the range from about 180 nm to 400 nm. "Coatable composition" means a liquid composition that can be applied to a substrate and thereafter solidified (e.g., by UV curing) to form a hardened coating on the substrate. "Radiation curable", in referring to the coatable compositions, means that the coatable composition will form a hardened coating upon exposure to radiation such as UV radiation or visible light (e.g., 180 to 800 nm). "Substrate" refers to any surface upon which the coatable compositions of the invention are applied and includes without limitation, vinyl floor tiles (including

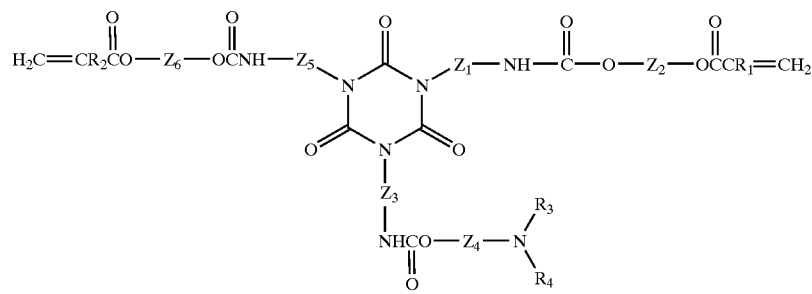

wherein
$R_1$ and $R_2$ are H or $CH_3$;
$R_3$ and $R_4$ may independently be alkyl groups (straight, branched or cyclic) having from 1 to 12 carbon atoms, tiles previously coated with floor sealer or the like), ceramic tiles, wood, marble, and the like. As used herein, "acrylate" will be understood to include acrylate and methacrylate species. "Monomer" refers to any chemical species having at least one free radical polymerizable group (e.g., acrylate, methacrylate). "Tertiary amine alcohol" is meant to indicate a tertiary amine that includes alcohol functionality.

In another aspect, the invention provides a floor finishing system, comprising the radiation curable coatable composition described above and a primer composition, the primer composition coatable over a substrate. In this aspect of the invention, the coatable composition is as previously described. The primer preferably comprises an acrylated latex with a solids content in water between about 2 and about 40% by weight. The latex is applied to the substrate and dried prior to the application of the coatable composition. The primer provides a layer over the substrate to which the coatable composition may bond. Moreover, the cured coatable composition is readily strippable from the substrate when the latex primer is present.

In still another aspect of the invention, a method for applying a protective coating to a substrate, comprising:
(A) applying a radiation curable coatable composition to a substrate, the composition comprising:
 (i) a first monomer comprising (a) polyfunctional isocyanurate having at least three terminal reactive groups reacted with (b) hydroxyalkyl acrylate and (c) tertiary amine alcohol in a molar ratio of a:b:c of about 1:1–2.5:0.5–2, wherein b+c is at least 3 and no greater than the total number of terminal reactive groups of (a),
 (ii) a second monomer, and
 (iii) photoinitiator; and
(B) hardening the composition to form a protective coating over the substrate by exposing the coatable composition to ultraviolet radiation.

In this aspect of the invention, the first monomer, the second monomer and the photoinitiator are as previously described. Overall, the coatable composition is preferably comprises at least about 90% solids (e.g., less than about 10% solvent). Hardening of the composition in step (B) may be achieved in air at prevailing temperature and humidity (e.g., at ambient conditions). Although high intensity radiation achieves faster curing of the coatable composition and is generally preferred in performing the hardening step (B), the coatable compositions can also be cured with low intensity UV radiation. Hardening of the coatable compositions at low UV intensities can be accomplished fairly quickly (e.g., less than 30 seconds) using a low intensity radiation source that provides at least one band of wavelengths less than about 300 nm and a second band between about 300 and 400 nm. Preferably, such a low intensity radiation source emits a first band of wavelengths centered around 254 nm and a second band centered between 350 and 370 nm (e.g., around 365 nm) to cure the coating (typically about 0.03 mm thick) in less than about 30 seconds. A suitable low intensity radiation source is one that provides a radiation intensity between about 5 and 15 mW per square centimeter. Preferably, the exposure of the coating to the low intensity radiation is for a period of up to about 30 seconds.

The foregoing method may also comprise, prior to the foregoing applying step (A), applying a primer composition to the floor and drying the primer composition to form a primer coat over the substrate. As discussed above, the preferred primer composition is an acrylated latex, preferably having a solids content between about 2 and about 40% by weight.

In still another aspect, the invention provides a coating derived from the foregoing radiation curable coatable composition. In another aspect, the invention provides a substrate coated with the aforementioned coating.

In still another aspect, the invention broadly provides a method for applying a protective coating to a substrate, comprising:
(a) applying a coatable acrylated latex primer composition to the substrate;
(b) drying the primer composition to form an acrylated polymer primer coat over the substrate;
(c) applying a radiation curable coatable composition to the primer coat; and
(d) hardening the radiation curable coatable composition by exposing the composition to ultraviolet radiation to form a protective coating over the substrate.

The details of the invention will be more fully appreciated by those skilled in the art upon consideration of the remainder of the disclosure including the detailed description of the preferred embodiment and the appended claims.

DETAILED DESCRIPTION OF THE PREFERRED EMBODIMENT

The preferred embodiment of the invention will now be described. It will be appreciated that the preferred embodiment, while illustrative, is not to be construed as unduly limiting the scope of the invention.

Coatable compositions according to the invention are formulated with a first monomer comprising an isocyanurate. The preferred first monomer is derived from the reaction of a polyfunctional isocyanate, hydroxyalkyl acrylate and tertiary amine alcohol. The compositions of the invention also comprise a second monomer and photoinitiator.

The individual components used in the formulation of the coatable composition will now be described.
First Monomer In the formulation of radiation curable coatable compositions usable as floor finishes, it is desired that the end product (e.g., the final hardened coating) be substantially free of observable color, provide a hard and durable finish, and be readily removable from the substrate to which the composition has been applied. To this end, it has been found that compositions comprising a certain class of polyfunctional isocyanurates will provide the desired coating.

The first monomer is preferably prepared from the reaction of polyfunctional isocyanaurate, (hydroxyalkyl) dialkylamine, and a hydroxyalkyl acrylate. In the reaction, about one mole of polyfunctional isocyanurate is reacted with from about one to about 2.5 moles of the hydroxyalkyl acrylate and with from about 0.5 to about 2.0 moles of the tertiary amine alcohol. As a result of the forgoing preparation, the first monomer comprises (a) polyfunctional isocyanurate having about three terminal reactive groups reacted with (b) hydroxyalkyl acrylate and (c) tertiary amine alcohol in a molar ratio of a:b:c of about 1:1–2.5:0.5–2, wherein b+c is at least 3 and no greater than the total number of terminal reactive groups of (a). The terminal reactive groups of the polyfunctional isocyanurate comprise isocyanate groups (—NCO), each of which is capable of reacting with the hydroxyl groups in both the hydroxyalkyl acrylate and the tertiary amine to form a urethane linkage (—NH—CO—O—) within the reaction product. Although the theoretical functionality of the polyfunctional isocyanurate is three, it will be appreciated the actual functionality of the polyfunctional isocyanurate may be somewhat less (e.g. between 2.5 and 3.0) while still being within the scope of the present invention.

As a result of the foregoing reaction, the first monomer may comprise a compound having the general formula:

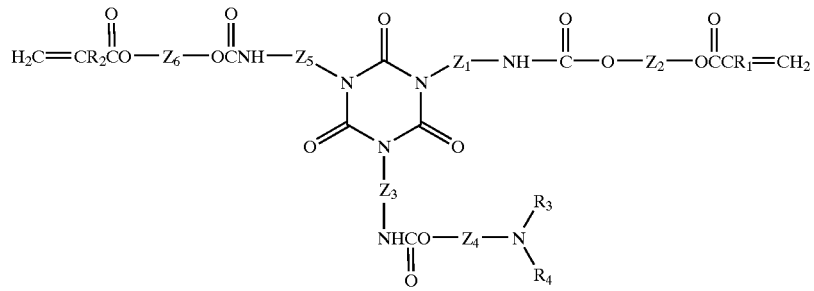

$R_1$ and $R_2$ are H or $CH_3$;

$R_3$ and $R_4$ may independently be alkyl groups (straight, branched or cyclic) having from 1 to 12 carbon atoms, or $R_3$ and $R_4$ may together form a divalent cylcoalkanediyl, oxacycloalkanediyl, or azacycloalkanediyl bridging group having from 2 to 12 carbon atoms; and $Z_1$, $Z_2$, $Z_3$, $Z_4$, $Z_5$, and $Z_6$ independently represent divalent groups having from 1 to 18 carbon atoms, preferably alkanediyl groups (straight, branched or cyclic) having from 1 to 18 carbon atoms, most preferably, straight chain alkanediyl groups having from 1 to 4 carbon atoms;

The polyfunctional isocyanate trimer useful in the formation of the polyfunctional isocyanurate preferably is a low viscosity polyfunctional aliphatic polyisocyanate resin. Preferably, the polyfunctional isocyanurate is a trimer of aliphatic diisocyanate and more preferably is a trimer derived from hexamethylene diisocyanate (HDI). In formulating the first monomer, it has been found that the foregoing polyfunctional isocyanurate is important in the formation of clear and substantially colorless coatings by UV curing. Moreover, compositions based on these polyfunctional isocyanurates typically cure rapidly (e.g., less than a minute) in air upon exposure to low intensity UV light.

Suitable polyfunctional isocyanurate may readily be synthesized by the oligomerization of diisocyanate (e.g., HDI) to provide the foregoing trimer, as is known to those skilled in the art. Suitable products based on HDI derived isocyanurate are commercially available such as those available under the trade designation DESMODUR N-3300. In addition, allophanated trimers derived from the reaction of HDI and butanol are suitable for use in the invention and are commercially available under the trade designations DESMODUR XP 7100 and DESMODUR XP 7040. The above-mentioned isocyanate trimers are available from the Industrial Chemicals Division of Bayer Corporation, Pittsburgh, Pa. It is preferred that the amount of allophanate be minimized for better performance of the resulting cured coating. Low viscosity aliphatic isocyanate diluents may be used in a similar manner, subject to the same requirements. To provide a preferred combination of performance characteristics in the finished coating and reduced viscosity in the coatable composition, the DESMODUR XP 7100 monomer is most preferred.

The polyfunctional isocyanurate used herein provides three distinct reactive isocyanate groups extending from the isocyanurate ring. Each of the isocyanate functionalities is capable of reacting with the hydroxyl group on both the tertiary amine alcohol and the hydroxyalkyl acrylate to form the first monomer.

Tertiary amine alcohols suitable for use in the invention include acyclic (hydroxyalkyl)dialkylamines having from 3 to 30 carbon atoms such as N,N-dimethylaminoethanol, N,N-dimethylaminopropanol, N,N-dimethylaminobutanol, N,N-dimethylaminohexanol, N,N-dimethylaminododecanol, N,N-diethylaminoethanol, N,N-diethylaminopropanol, N,N-diethylaminobutanol, N-ethyl-N-methylaminopropanol, N-ethyl-N-hexylaminoethanol, and the like; alicyclic (hydroxyalkyl)dialkylamines having from 3 to 30 carbon atoms such as 2-aziridinylethanol, 2-azetidinylethanol, 2-piperidinoethanol, N-methyl-4-azacyclohexanol, and the like; polyaminoalcohols having from 3 to 30 carbon atoms such as N-methylpiperazinoethanol, N-butylpiperazinoethanol, N-methylpiperazinobutanol, and the like. (Hydroxyalkyl) alkylarylamines and (hydroxyalkyl)diarylamines may also be used in the invention, although their use is not preferred due to the tendency of compositions comprising aromatic amines to discolor upon curing. Tertiary amine alcohols including the foregoing examples thereof, may be synthesized according to known methods, or they may be commercially obtained from any of a variety of commercial sources such as Texaco Corp. of Houston, Tex.; Ashland Chemical Co. of Columbus, Ohio and Aldrich Chemical Co. of Milwaukee, Wis.

In addition to the foregoing tertiary amine alcohols, about two moles of the hydroxyalkyl acrylate is reacted with about one mole of polyfunctional isocyanurate. The hydroxyl group of the hydroxyalkyl acrylate reacts with isocyanate so that the main reaction product comprises acrylate groups pendant to the isocyanurate ring. The double bonds of these acrylate groups provide reactive sites capable of forming additional bonds with other monomers during polymerization. Suitable hydroxyalkyl acrylate compounds comprise any of a variety of acrylic compounds including hydroxyalkyl acrylates, N-hydroxyalkyl acrylamides, and the like. Preferred are the hydroxyalkyl acrylates, especially hydroxyalkyl acrylates comprising a $C_1$ to $C_4$ hydroxyalkyl moiety. A particularly preferred hydroxyalkyl acrylate is 2-hydroxyethyl acrylate, available from Dow Chemical Co. of Midland, Mich.

Second Monomer

The foregoing first monomer may be polymerized in a reaction with at least one additional radiation curable monomer ("second monomer"). In the presence of a suitable amount of photoinitiator and upon exposure to ultraviolet radiation, the first monomer and the second monomers react to form a highly cross-linked polymeric coating suitable for use as a floor finish or the like.

The second monomer can be selected from any of a variety of radiation sensitive polymerizable monomers including mono-, di- and tri-functional acrylates, as well as acrylates of higher functionality and combinations of the foregoing. Preferably, the second monomer is selected from di- or tri-functional acrylates and combinations thereof Suitable di- or tri-functional acrylates are commercially available from Sartomer Company, Inc. of West Chester, Pa. The second monomer(s) is chosen to achieve a preferred balance of properties in both the uncured composition as well as in the cured coating. Suitable acrylates for use in the invention include, without limitation, monoacrylates such as tetrahydrofurfuryl acrylate, cyclohexyl acrylate, n-hexyl acrylate, 2-ethoxyethyl acrylate, isodecyl acrylate, 2-methoxyethyl acrylate, 2-(2-ethoxyethoxy)ethyl acrylate, stearyl acrylate, lauryl acrylate, octyl acrylate, 2-phenoxyethyl acrylate, glycidyl acrylate, isobornyl acrylate, benzyl acrylate, tridecyl acrylate, caprolactone acrylate, ethoxylated nonylphenol acrylate, polypropylene glycol acrylate, and the like; diacrylates such as triethylene glycol diacrylate, ethylene glycol diacrylate, tetraethylene glycol diacrylate, polyethylene glycol diacrylate, 1,3-butylene glycol diacrylate, 1,4-butanediol diacrylate, diethylene glycol diacrylate, hexanediol diacrylate, neopentyl glycol diacrylate, tripropylene glycol diacrylate, ethoxylated bisphenol A diacrylate, propoxylated neopentyl glycol diacrylate, and the like; triacrylates such as trimethylolpropane triacrylate, tris(2-hydroxyethyl)isocyanurate triacrylate, ethoxylated trimethylolpropane triacrylate, pentaerythritol triacrylate, propoxylated trimethylolpropane triacrylate, propoxylated glyceryl triacrylate, and the like; higher functionality acrylates such as pentaerythritol tetraacrylate, ditrimethylolpropane tetraacrylate, ethoxylated pentaerythritol tetraacrylate, and the like; metallic acrylates such as zinc diacrylate, calcium diacrylate and the like; acrylated oligomers and polymers such as polyurethane mono- and poly-acrylates, polyester mono- and poly-acrylates, polyamide mono- and poly-acrylates, polybutadiene mono- and poly-acrylates, and the like; and, acrylated silicones such as those available under the trade designations "EBECRYL 350" or "EBECRYL 1360" from UCB Radcure of Smyrna, Ga.

The second monomer may comprise substances other than acrylated monomers, preferably substances that readily copolymerize with acrylate monomers such as the foregoing acrylated first monomer used in the present invention. Suitable materials include N-vinyl monomers such as N-vinylformamide, N-vinylpyrrolidone, N-vinylcarbazole, and the like; acrylamide and derivatives thereof such as methylolacrylamide; styrenic monomers such as styrene, a-methylstyrene, vinylpyridine, and the like; and other monomers such as vinyl ethers, allyl ethers such as triallyl isocyanurate, allyl acrylate and ether maleate esters, for example.

Acrylated substances are preferred for use as the second monomer herein. Most preferred are ethoxylated trimethylolpropane triacrylates such as those commercially available from Sartomer Company under the trade designations "SR 454", "SR 499", "SR 502" and "SR 9035" and propoxylated diacrylates such as tripropylene glycol diacrylate.

As mentioned, the second monomer(s) is added to a reaction mixture with the first monomer and polymerized to form the hard, durable, clear coatings of the invention, as is further described below. In the reaction mixture, the weight percentage of the second monomer is typically within the range from about 5 to about 90%, preferably from about 35 to about 70 wt % and more preferably from about 45 to about 65 wt %. The first monomer is present within the mixture at a concentration within the range from about 10 to about 90 wt %, preferably from about 25 to about 60 wt %, and more preferably from about 30 to about 50 wt %.

Photoinitiator

As mentioned, photoinitiator is added to the compositions of the invention to initiate the polymerization reaction. Preferred photoinitiators are free radical initiators for ultraviolet curing. In the selection of a suitable photoinitiator for use in the present invention, special attention is given to the properties of high molar absorptivity (e.g., extinction coefficient) at the power maxima for the light source, low color and low tendency to color after UV exposure, shelf life stability, low or pleasant odor and high efficiency for photoinitiation of polymerization. In order to achieve a rapid and satisfactory cure of the compositions of the invention, the photoinitiator will preferably have a high molar absorptivity (e.g., greater than 10,000 liter/mole-cm) at one wavelength of the light source, while having a lesser molar absorptivity at another or second wavelength of the light source (e.g., less than 10,000 liter/mole-cm). Preferably, the compositions of the invention will contain photoinitiators in concentrations such that the absorbance for a 25 micron film will be greater than or equal to about 2.5 at one wavelength (typically 254 nm) to assure a rapid surface cure, while the absorbance at the longer wavelength (typically 350–370 nm) will be from about 0.05 to about 0.8, and more preferably from about 0.4 to about 0.6 to ensure a rapid and effective through cure.

The photoinitiators useful in the invention include those known as useful in the UV cure of acrylate polymers. Such initiators include benzophenone and its derivatives; benzoin, α-methylbenzoin, α-phenylbenzoin, α-allylbenzoin, α-benzylbenzoin; benzoin ethers such as benzil dimethyl ketal ((commercially available under the trade designation "IRGACURE 651" from Ciba-Geigy of Ardsley, N.Y.), benzoin methyl ether, benzoin ethyl ether, benzoin n-butyl ether; acetophenone and its derivatives such as 2-hydroxy-2-methyl-1-phenyl-1-propanone (commercially available under the trade designation "DAROCUR 1173" from Ciba-Geigy of Ardsley, N.Y.) and 1-hydroxycyclohexyl phenyl ketone (HCPK) (commercially available under the trade designation "IRGACURE 184", also from Ciba-Geigy Corporation); 2-methyl-1-[4-(methylthio)phenyl]-2-(4-morpholinyl)-1-propanone commercially available under the trade designation "IRGACURE 907", also from Ciba-Geigy Corporation); 2-benzyl-2-(dimethlamino)-1-[4-(4-morpholinyl)phenyl]-1-butanone commercially available under the trade designation "IRGACURE 369", also from Ciba-Geigy Corporation). Other useful photoinitiators include pivaloin ethyl ether, anisoin ethyl ether; anthraquinones such as anthraquinone, 2-methylanthraquinone, 2-ethyl anthraquinone, 2-t-butyl anthraquinone, 1-chloroanthraquinone, 2-bromoanthraquinone, 2-nitroanthraquinone, anthraquinone-1-carboxaldehyde, anthraquinone-2-thiol, 4-cyclohexylanthraquinone, 1,4-dimethylanthraquinone, 1-methoxyanthraquinone, benzathraquinonehalomethyl triazines; onium salts, for example, diazonium salts such as phenyldiazoniumhexafluorophosphate and the like; diaryliodonium salts such as ditolyliodonium hexafluoroantimonate and the like, sulfonium salts such as triphenylsulfonium tetrafluoroborate and the like; titanium complexes such as bis($\eta_5$-2,4-cyclopentadien-1-yl)bis[2,6-difluoro-3-(1H-pyrrol-1-yl)phenyl]titanium commercially available under the trade designation "CGI 784 DC", also from Ciba-Geigy Corporation); uranyl salts such as uranyl nitrate, uranyl propionate; halomethylnitrobenzenes such as 4-bromomethylnitrobenzene and the like; mono- and bis-acylphosphines such as those available from Ciba-Geigy under the trade designations "IRGACURE 1700", "IRGACURE 1800", "IRGACURE 1850" and "DAROCUR 4265". It is contemplated that other photoinitiators not listed herein may also be suitable for use in the present invention.

The selection of a suitable photoinitiator is well within the skill of those practicing in the field.

A preferred photoinitiator used in this composition is a combination of about 4 parts by weight benzophenone (based on the total weight of the composition) and 1 part by weight N-ethylcarbazole or N-vinylcarbazole. Another preferred photoinitiator is a combination of about 4 parts by weight benzophenone (based on the total weight of the composition) and 1 part by weight benzoin dimethyl ketal. Preferably, the photoinitiator is present in the compositions of the invention at a concentration between about 2 and about 10 wt % and more preferably between about 4 and about 7 wt %.

Other Ingredients

Additional optional components can be included within the coatable compositions of the invention. For example a wetting agent may be added in minor amounts to the coatable compositions to facilitate uniform coating over a suitable substrate. Suitable wetting agents include, for example, fluorinated agents such as those commercially available under the trade designations "FLUORAD FC-431" and "FLUORAD FC-171", both available from the Minnesota Mining and Manufacturing Company of St. Paul, Minn.

Fillers may be added to the coatable compositions of the invention to modify wear properties. Fillers known to be useful in acrylate clear coat applications may be used in the invention. A preferred filler is one in which silica particles are modified with 3-mercaptopropyltrimethoxysilane.

Other possible ingredients include defoamers, leveling aids, mar and slip additives, air release additives; antioxidants, light stabilizers such as benzotriazole light stabilizers, hydroxybenzophenone light stabilizers and the like; optical brighteners and other known formulation additives.

Preparation and Use of Coatable Compositions

In the preparation of the coatable compositions of the present invention, the first monomer is preferably prepared first and then blended with the second monomer(s), photoinitiator and other ingredients.

In the preparation of the first monomer, the polyfunctional isocyanurate is first added to a reaction vessel along with a suitable catalyst such as dibutyltin dilaurate. A mixture is prepared by the addition of the tertiary amine alcohol and the hydroxyalkyl acrylate. A suitable preservative that will not be consumed during the reaction such as, for example, butylated hydroxytoluene (BHT) may also be added to the reaction mixture. The mixture of tertiary amine alcohol, hydroxyalkyl acrylate and preservative are added to the reaction vessel (containing the first monomer). The reaction is allowed to proceed to completion under ambient conditions in air while controlling the temperature of the reaction mixture, preferably at a temperature below about 40° C. to prevent the premature consumption of the preservative. The reaction mixture is then allowed to cool to room temperature. Completion of the reaction may be monitored by appropriate means, such as by infrared spectrophotometry.

The thus prepared first monomer may then be combined in an appropriate reaction vessel with a second monomer, photoinitiator and other optional ingredients to provide the coatable compositions of the invention. A particularly preferred coatable composition according to the invention is one comprising about 42 parts by weight first monomer (preferably DESMODUR XP 7100 isocyanurate commercially available from Bayer Corporation), about 48 parts by weight of ethoxylated trimethylolpropane triacrylate (commercially available under the trade designation "SR-499" from Sartomer Company, Inc.), about 5 parts by weight of tripropylene diacrylate, about 5 parts by weight photoinitiator and about 0.3 parts by weight of a suitable wetting agent (e.g., FLUORAD FC-171 from Minnesota Mining and Manufacturing Company), and about 0.5 parts of the acrylated silicone EBECRYL 350 commercially available from UCB Radcure of Smyrna, Ga.

In order to prolong storage of the compositions of the invention inhibitors may be added. Suitable inhibitor may be any material known to inhibit free-radically induced polymerization including, but not limited to hindered phenols such as butylated hydroxytoluene (BHT) and its derivatives, hydroquinone and its derivatives such as methylhydroquinone, and N-nitrosophenylhydroxylamine aluminum salt commercially available under the designation "Q-1301" from Wako Chemicals USA, Inc. (Richmond, Va.). Of these N-nitrosophenylhydroxylamine aluminum salt is preferred.

The composition may then be coated onto a suitable substrate such as a conventional polyvinyl chloride floor tile, for example. Once coated over the substrate, the coatable composition is exposed to UV light to cure the composition to a hardened protective coating. Suitable light sources may be selected by those skilled in the art. In general, high intensity light sources are preferred to achieve a fast cure of the coatable composition. However, in the application of the coatable compositions to installed flooring, low intensity UV light may be more practical, and the coatable compositions of the invention are readily curable by brief exposure to low intensity UV light. In general, a suitable low intensity UV light source is one that emits at least one band of wavelengths less than about 300 nm. To achieve a faster cure of the applied coating, the light source will preferably also emit a second band of wavelengths between about 300 and 400 nm. It has been found that for coating thicknesses of about 0.03 mm, a UV light source that emits a narrow band of wavelengths centered around 254 nm at an intensity (at the surface of the coating) of approximately 5–15 mW per square centimeter is adequate. Preferably, such a low intensity light source also emits a second narrow band of wavelengths centered in the range 360–370 nm and typically around 365 nm at the same approximate intensity as mentioned. At the foregoing low level UV intensity, the compositions of the present invention will normally-cure in less than 30 seconds, preferably in less than 20 seconds. One such light source is that described below in the Examples.

It will be appreciated that the overall configuration of the light source is outside the scope of the invention. Different light sources may be used to effect curing of the compositions of the invention such as a pulsed xenon flash source, a medium pressure mercury source, a low pressure mercury fluorescent source and a 300 nm fluorescent source. It is also contemplated that longer wavelength lamps could be used to initiate the polymerization reaction if a suitable photoinitiator is used.

In applying the coatable compositions of the invention to a suitable substrate, it is preferred that the composition be applied in manner which creates a coating no greater than about 1.3 millimeters in thickness in order to facilitate curing of the composition within the aforementioned time limits. Coatings of this thickness can be achieved by any of a number of known application techniques such as roll coating, squeegeeing, knife coating, curtain coating, spray coating, and the like. In applying the forgoing compositions to a substrate, suitable substrates include conventional floor tiles which may or may not be previously coated or sealed. When the substrate to be coated is vinyl tile or the like, it is preferred that the substrate is first treated with a primer or sealer prior to the application of the UV curable inventive compositions to that substrate. A primer treatment of the substrate facilitates the ease at which the UV cured coating may subsequently be removed from the tile or other substrate by a chemical stripping formulation, for example. In order to promote adhesion of the coatable composition to the substrate, an acrylated latex primer is most preferred. The acrylated latex compositions useful herein must have at least one free-radically polymerizable group pendant from each latex particle, and preferably more than one. The latex is hydrophobic in nature, but may contain some hydrophilic groups.

When applying the primer to the substrate, it is desirable to provide a continuous film over the surface of the substrate, adjusting the solids content of the primer as needed to achieve such a film while using the least amount of primer required to achieve a barrier layer with the desired adhesion properties. Typically, the solids content of the primer required for a wipe on coating (e.g., by hand) will be between about 2 and about 40% by weight, preferably between about 2 and about 20%, and more preferably between about 4 and about 15%. A wetting agent or defoamer may be added to. the latex emulsion to improve coating properties. The level of such additives will depend on the nature of the substrate and the concentration of the latex emulsion.

One preferred latex emulsion for use as a primer herein is the acrylated emulsion commercially available under the trade designation "ROSHIELD 3120" from Rohm and Haas Company, Philadelphia, Pa. This emulsion is available at a solids content of about 40.5% by weight, and a suitable primer can be prepared by dilution of the concentrated emulsion at a dilution weight ratio of up to about 9:1 (water:emulsion). More preferred is an aqueous primer formulation comprising a blend or the foregoing ROSHIELD 3120 acrylated latex with a second primer polymer, preferably the ammonium salt of a styrene maleic anhydride (SMA) copolymer (commercially available at a solids content of 38.5% under the trade designation "SMA 1000A" from Atochem, Inc. of Malvern, Pa.). The SMA is added to the primer to act as a leveling aid. The weight ratio of the acrylate to the SMA copolymer in the primer is preferably between about 7:1 and about 12:1 and more preferably is about 10:1. A small amount of surfactant may also be included in the primer. A particularly preferred primer, having a solids content of about 10% by weight, comprises about 24.4 wt % of the ROSHIELD 3120 acrylated latex, about 73.2 wt % water, about 2.4 wt % SMA 1000A copolymer and about 0.02 wt % surfactant or wetting agent such as that commercially available under the trade designation "FLUORAD FC-129" from Minnesota Mining and Manufacturing Company, St. Paul, Minn.

The primer may be applied to the substrate by any suitable method such as wiping, brushing, spraying and the like. The latex is allowed to dry, typically under ambient conditions, and the UV curable compositions of the invention may then be applied thereover and cured, as described herein. Substrates such as PVC tiles, for example, coated with the above acrylated latex primer and then coated with a UV curable acrylate (e.g., a coatable composition) may be readily stripped using a benzyl alcohol stripper such as that described below in the Examples. The thus stripped tiles present a very good appearance with stripping appearing to occur at the surface of the tile. Corresponding unprimed tiles coated with the same UV curable acrylate are slower to strip and generally do not strip cleanly (e.g., at the substrate surface).

In the above described aspect of the invention, the primer can comprise a component of a floor finishing system that includes both the primer as well as the coatable composition described herein. Although primers comprising the foregoing, ROSHIELD 3120 acrylated latex (with or without added SMA copolymer) are preferred, other commercially available materials may also be used as primers on certain substrates such as on PVC composition floor tile. Some suitable primers include various commercial floor sealers such as those available under the trade designations "CORNERSTONE" (Minnesota Mining and Manufacturing Company, St. Paul, Minn.), "TOPLINE" (also from Minnesota Mining and Manufacturing Company) and "TECHNIQUE" (S. C. Johnson of Milwaukee, Wis.). It is also contemplated that the foregoing primer, especially primers comprising ROSHIELD 3120 acrylated latex, may be used in other applications outside the floor finishing art to apply any of a variety of UV polymerizable polymers (e.g., other than the foregoing coatable compositions) to a substrate. Accordingly, the use of the primer provides a system and a method for coating a variety of substrates with a UV curable polymer. In such a system and method, the resulting coatings adhere well to the substrate and may also be more easily removed from the substrate by suitable stripper compositions. When using a non-acrylated latex primer it is preferable to use a primer which has a surface tension of at least 40 dynes/cm.

The cured coatings of the invention may be stripped from the substrates to which they are applied by the application of a suitable stripper. Preferably, the stripper is a pH neutral formulation comprising a solvent, coupling agent (e.g., hydrotrope) and water. Dye, fragrance and thickening agent may be added to the stripper composition if desired. An effective stripper formulation for the floor finish compositions of the invention includes those set forth below in the Test Methods.

EXAMPLES

Materials

Ingredients used in the Examples below are identified as follows:

| | |
|---|---|
| DESMODUR N3300 | is the trade designation for a hexane diisocyanate trimer available from Bayer Corp., Industrial Chemicals Division. |
| DESMODUR XP 7100 | is the trade designation for an allophanated hexane diisocyanate trimer mixture available from Bayer Corp., Industrial Chemicals Division. |
| DESMODUR XP 7040 | is the trade designation for an allophanated hexane diisocyanate trimer mixture available from Bayer Corp., Industrial Chemicals Division. |
| SR 306 | is the trade designation for tripropylene glycol diacrylate, a difunctional acrylate monomer commercially available from Sartomer Co., Inc. of West Chester, PA. |
| SR 335 | is the trade designation for lauryl acrylate, a monofunctional acrylate monomer commercially available from Sartomer Co., Inc. of West Chester, PA. |
| SR 454 | is the trade designation for ethoxylated trimethylolpropane triacrylate a trifunctional acrylate monomer commercially available from Sartomer Co., Inc. of West Chester, PA. |

-continued

| | |
|---|---|
| SR 499 | is the trade designation for ethoxylated trimethylolpropane triacrylate a trifunctional acrylate monomer commercially available from Sartomer Co., Inc. of West Chester, PA. |
| DAROCUR 1173 | is the trade designation for 2-hydroxy2-methyl-1-phenylpropan-1-one, a photoinitiator commercially available from Ciba-Geigy, Ardsley, New York. |
| DAROCUR 4265 | is the trade designation for an acylphosphine photoinitiator commercially available from Ciba-Geigy, Ardsley, New York. |
| IRGACURE 184 | is the trade designation for 1-hydroxycyclohexyl phenyl ketone, a photoinitiator commercially available from Ciba-Geigy Corporation, Ardsley, New York. |
| FLUORAD FC-431 | is the trade designation for a wetting agent available from Minnesota Mining and Manufacturing Company, St. Paul, Minnesota. |
| FLUORAD FC-171 | is the trade designation for a wetting agent available from Minnesota Mining and Manufacturing Company, St. Paul, Minnesota. |
| PVC Tile | refers to standard floor tile comprising polyvinyl chloride that has been stripped and cleaned to remove the factory finish. |
| Sealed PVC Tile | refers to standard floor tile comprising polyvinyl chloride that has been stripped and cleaned to remove the factory finish and then coated with a floor finish or sealer. |
| ROSHIELD 3120 | is the trade designation for an acrylated emulsion commercially available from Rohm and Haas Company, Philadelphia, PA at a solids content of 40.5% by weight, and used herein as a primer by dilution of the concentrate with water at a dilution ratio of 9:1 (water:emulsion). |
| EBECRYL 350 | is the trade designation for acrylated silicones commercially available from UCB Radcure of Smyrna, Georgia. |
| TECHNIQUE | is the trade designation for an acrylic floor sealer commercially available from S. C. Johnson, Milwaukee, Wisconsin. |
| TOPLINE | is the trade designation for an acrylic floor finish commercially available from Minnesota Mining and Manufacturing Company, St. Paul, Minnesota. |
| CORNERSTONE | is the trade designation for an acrylic floor finish commercially available from Minnesota Mining and Manufacturing Company, St. Paul, Minnesota. |

Preparative Procedures

The following procedures were used in the preparation of materials described in the Examples.

Preparation of Oligomer A

A dry five-liter reaction vessel was fitted with a drying tube, addition funnel, thermometer and mechanical stir and charged with 450.0 g (2.30 eq) of hexane diisocyanate trimer (DESMODUR N 3300). Four drops of dibutyltin dilaurate were added to the reaction vessel. A mixture was prepared by mixing 68.43 g 2-(N,N-dimethylamino)ethanol (0.77 eq.), 178.3 g 2-hydroxyethyl acrylate (1.54 eq.) and 0.35 g methylhydroquinone as a preservative. This mixture was added to the reaction vessel while maintaining the temperature of the contents below 35° C. When the mixture had cooled to room temperature it was isolated by pouring it into a container. Infrared analysis indicated only trace amounts of isocyanate or free alcohol present. This material was very viscous, requiring a spatula to dispense.

Preparation of Oligomer B

A dry five-liter reaction vessel was fitted with a drying tube, addition funnel, thermometer and mechanical stir and charged with 600.0 g (2.93 eq.) of allophanated hexane diisocyanate trimer (DESMODUR XP 7100). A mixture was prepared by mixing 87 g 2-(N,N-dimethylamino)ethanol (0.975 eq.), 226.7 g 2-hydroxyethyl acrylate) (1.95 eq.) and 0.45 g BHT as a preservative. 9 drops dibutyltin dilaurate were added to the reaction vessel. The mixture was added to the reaction vessel while maintaining the temperature of the mixture below 30° C. When the mixture had cooled to room temperature it was isolated by pouring it into a container. Infrared analysis indicated only trace amounts of isocyanate or free alcohol present. This material was moderately viscous and difficult to pour.

Preparation of Oligomer C

A dry one-liter reaction vessel was fitted with a drying tube, addition funnel, thermometer and mechanical stir and charged with 642 g (3.018 eq.) allophanated hexane diisocyanate trimer (DESMODUR XP 7040). 6 drops dibutyltin dilaurate were added to the reaction vessel. A mixture was prepared by mixing 89.7 g 2-(N,N-dimethylamino)ethanol (1.01 eq.), 233.7 g 2-hydroxyethyl acrylate (2.012 eq.) and 0.48 g BHT as a preservative. This mixture was added to the reaction vessel while maintaining the temperature of the contents below 40° C. When the mixture had cooled to room temperature it was isolated by pouring it into a container. Infrared analysis indicated only trace amounts of isocyanate or free alcohol present. This material had low viscosity and was easily pourable.

Preparation of Modified Silica Particles

Mercapto-functionalized silica was prepared. 1176 grams of an aqueous dispersion of colloidal silica having a solids content of 34 wt % at a pH of 3.2 (commercially available from Nalco Chemical Company of Naperville, Ill. under the trade designation NALCO 1042) was diluted to 10% total solids with distilled water to give 4000 g total. To this was added 19.6 g of (3-mercaptopropyl)trimethoxysilane (available from Aldrich Chemical Company, Milwaukee, Wis.). The resulting suspension was heated for 18 hours at 80° C. with stirring to give a translucent, colorless suspension which was used without purification. A portion of the above suspension (50 g) was mixed with 45 g SR 499 to give a slurry. The water was removed under vacuum (aspirator/rotovap) at room temperature to give 50 g of a clear liquid.

General Procedures

Curing Procedure A

UV exposures were made using a wheeled cart capable of running off 110 V power having a front mounted downward facing bank of 18 inch (45.7cm) fluorescent lights on 1.5 inch (3.81 cm) centers at a distance of approximately 1 inch (2.54 cm) from the floor. The lights were cantilevered in front of the cart wheels to allow for forward motion over uncured floor coating without marring the finish. A reflective aluminum sheet was mounted behind the lights to boost the radiant energy directed toward the coating. The lamps were in two sets within the bank. The first set consisted of two 15 watt lights on a 25 watt ballast in the front of the bank. These two lights consisted of one (1) 15 watt germicidal light (a low pressure mercury light emitting at about 254 nm) and one (1) 15 watt blacklight (365 nm). The second set consisted of six (6) 15 watt lights on a 15 watt ballast. The second set was positioned in the bank with a two inch gap between the two light sets. The second light set consisted of alternating germicidal and blacklights for a total of six (6) lights in the second set.

All of the germicidal bulbs were commercially available from General Electric under the designation "F15T8". The blacklight bulbs were also available from General Electric under the designation "F15T8/BL". Power measured at the germicidal bulb surface in the bulb center was about 11 mW/cm$^2$ for the 25 watt ballast and about 7 mW/cm$^2$ for the 15 watt ballast. Power measured at the blacklight bulb surface in the bulb center was about 7 mW/cm$^2$ for the 25 watt ballast and about 4.5 mW/cm$^2$ for the 15 watt ballast.

Unless otherwise indicated, all samples were cured in a 30 second exposure to the above light source.

Curing Procedure B

Exposures were made using a downward facing bank of 18" fluorescent lights on 1.5 inch centers at a distance of approximately 1 inch from the floor. A reflective aluminum sheet was mounted behind the lights to boost the radiant energy director toward the coating. The light set consisted of six germicidal bulbs.

All of the bulbs were commercially available from General Electric under the designation "T15T8". Power measured at the bulb surface in the bulb center was about 7 mW/cm$^2$.

Unless otherwise indicated, all samples were cured in a 30 second exposure to the above light source.

Coating Procedure A

In applying the coatable compositions to a substrate such as PVC Tile or Sealed PVC Tile, a small volume of the composition, typically about 2–3 grams, was applied to the substrate using a syringe. The thus applied composition was then coated over the substrate by using a hand held rubber roller to roll the composition over the desired area of the substrate until a fairly uniform coating was obtained over the desired area of the substrate. The composition was then cured. To determine the coating weight, the weight of the coated tile was compared to the initial tile weight (e.g., before applying the coatable composition).

Test Methods

In the Examples which follow, the following test methods were employed.

Test Method A (Taber Abrasion Resistance)

A 4"×4" square sample of coated material to be tested was prepared. Using a template to precisely locate a spot on the coating where the abrasion was expected to occur, an initial 20° or 60° gloss reading was obtained for each side (four readings total) using a Byk-Gardner Micro-Tri-Gloss meter (Byk-Gardner, Silver Spring, Md.). The sample was then mounted on a Taber Standard Abrasion Tester (model no. 503, Teledyne Taber, North Tonawanda, N.Y.) fitted with a vacuum attachment, 500 g wheel weights and CS-10f wheels. The sample was subjected to 100 revolutions and the gloss after abrasion was measured as before. The percent gloss retention for each side was calculated, and the results were averaged.

Test Method B (Scratch Hardness)

Scratch hardness was determined using a Byk-Gardner pencil-type scratch tester (Byk-Gardner, Silver Spring, Md.). Measurements were reproducible to about±100 g. The results were generally substrate and film thickness dependent.

Test Method C (Strip Time)

In testing the coatings of the invention to determine the amount of time required to strip a radiation-cured coating from a substrate, the following formulation was used to strip coatings from tile substrates: 68.75 parts deionized water, 22.50 parts benzyl alcohol, 5.52 parts n-octylamine, 3.24 parts glycolic acid, 0.02 parts surfactant ("FLUORAD FC-129" from Minnesota Mining and Manufacturing Company).

The stripper was applied by a dropper onto a cured coating at numerous locations on the coating. The strip time recorded was the time at which either 1) the film bubbled up over the entire area covered with stripper; or 2) the time required for the stripper to sufficiently loosen the coating so that hand wiping of the applied stripper with a paper towel resulted in a clean stripped substrate surface. Condition 1 was generally observed for coatings applied over Sealed PVC Tile while condition 2 was generally observed for PVC Tile. The strip time is highly sensitive and will depend on coating thickness as well as the degree of cure for a particular coating. Consequently, care must be taken in comparing strip time results of coatings having different thicknesses or those that have experienced different degrees of cure.

Test Method D (Gloss Measurements)

Gloss measurements were made using a calibrated Byk-Gardner Micro-Tri-Gloss meter (Byk-Gardner, Silver Spring, Md.). Readings were taken following a cleaning of the surface.

Test Method E (Color Measurement)

Color measurements were made using a calibrated Datacolor International Microflash 200d spectrophotometer (Datacolor International, Charlotte, N.C.) in specular mode using a 1.5 cm aperture. All readings were an average of 3 measurements. CIELAB color coordinates L*, a*, b* and the color shift DE used herein are well known terms in color measurement.

EXAMPLES

The following non-limiting Examples illustrate the preparation, utility and the comparative advantages of the present invention. Unless otherwise indicated, all parts and percentages are by weight.

Examples 1–15

Examples 1–15 were prepared and evaluated for durability according to Test Method A. Analysis of the results indicates that formulations with reduced amounts of the SR-306 difunctional acrylate have the best durability. All samples contained 0.3 parts FC-431 FLUORAD wetting agent, and were coated onto PVC Tile. They were coated at 2.5 g/ft2 (26.9 g/m2) using Coating Procedure A and cured using Curing Procedure A. The formulations for these Examples and the abrasion resistance data are set forth in Table 1.

TABLE 1

Examples 1–15

| Formulation Example | Parts Oligomer A | Parts SR-499 | Parts SR-306 | Parts DAROCUR 1173 | % 20° Gloss Retention | Standard Deviation |
|---|---|---|---|---|---|---|
| 1 | 50.00 | 35.00 | 15.00 | 5 | 74.0 | 4.8 |
| 2 | 30.00 | 45.00 | 25.00 | 5 | 43.1 | 8.1 |
| 3 | 40.00 | 42.50 | 17.50 | 5 | 67.0 | 2.6 |
| 4 | 40.00 | 35.00 | 25.00 | 5 | 63.5 | 3.0 |
| 5 | 35.00 | 50.00 | 15.00 | 5 | 70.9 | 3.4 |
| 6 | 40.00 | 35.00 | 25.00 | 5 | 66.3 | 3.2 |
| 7 | 40.00 | 42.50 | 17.50 | 5 | 74.2 | 1.9 |
| 8 | 50.00 | 40.00 | 10.00 | 5 | 78.2 | 1.7 |
| 9 | 45.00 | 45.00 | 10.00 | 5 | 77.8 | 1.5 |
| 11 | 40.00 | 50.00 | 10.00 | 5 | 77.2 | 1.4 |
| 12 | 50.00 | 40.00 | 10.00 | 5 | 76.4 | 3.5 |
| 13 | 30.00 | 45.00 | 25.00 | 5 | 64.1 | 3.0 |
| 14 | 30.00 | 50.00 | 20.00 | 5 | 56.1 | 3.4 |
| 15 | 45.00 | 35.00 | 20.00 | 5 | 64.2 | 2.1 |

Example 16

A series of samples were prepared based in part on the above data for Examples 1–15. The Example 16 samples were made with 40 parts Oligomer A, 45 parts trifunctional acrylate (SR-499), 10 parts difunctional acrylate (SR-306), 0.3 parts wetting agent (FLUORAD FC-431) and photoinitiator. 5 parts of a photoinitiator such as the DAROCUR 1173 material or other photoinitators were all used successfully including 3 parts benzophenone combined with 2 parts of either DAROCUR 1173 photoinitiator or IRGACURE 184 photoinitiator. These compositions were coated over Sealed PVC Tile that had an applied primer coat of COR-NERSTONE floor sealer according to Coating Procedure A and cured according to Curing Procedure A. Abrasion resistance, scratch hardness, and strip times were determined according to the above Test Methods A, B and C. The % 20° gloss retention for these samples was consistently about 83%. Scratch hardness was about 1200 g. Strip time was less than 5 minutes.

Examples 17–30

Examples 17–30 were prepared and evaluated for abrasion resistance according to Test Method A. Analysis of the results indicates that formulations with reduced amounts of the SR-306 difunctional acrylate have the best durability. All samples contained 0.3 parts wetting agent (FLUORAD FC-431), and were coated onto PVC Tile, They were coated at 2.5 g/ft² (26.9 g/m²) using a Coating Procedure A and cured using Curing Procedure A. The compositions of the Examples and the abrasion resistance data are set forth in Table 2.

TABLE 2

Examples 17–30

| Formulation Example | Parts Oligomer B | Parts SR-499 | Parts SR-306 | Parts DAROCUR 1173 | % 20° Gloss Retention | Standard Deviation |
|---|---|---|---|---|---|---|
| 17 | 60 | 30 | 5 | 5 | 66.7 | 0.4 |
| 18 | 60 | 30 | 5 | 5 | 68.1 | 1.0 |
| 19 | 45 | 45 | 5 | 5 | 75.1 | 8.3 |
| 20 | 45 | 35 | 15 | 5 | 48.8 | 6.4 |
| 21 | 45 | 30 | 20 | 5 | 51.2 | 4.3 |
| 22 | 41.25 | 41.25 | 12.5 | 5 | 62.3 | 1.1 |
| 23 | 45 | 45 | 5 | 5 | 73.4 | 2.2 |
| 24 | 45 | 30 | 20 | 5 | 60.7 | 1.9 |
| 25 | 30 | 45 | 20 | 5 | 7.6 | 5.2 |
| 26 | 30 | 60 | 5 | 5 | 72.9 | 2.3 |
| 27 | 37.5 | 37.5 | 20 | 5 | 56.1 | 4.1 |
| 28 | 30 | 52.5 | 12.5 | 5 | 66.2 | 4.5 |
| 29 | 30 | 60 | 5 | 5 | 69.0 | 8.7 |
| 30 | 52.5 | 30 | 12.5 | 5 | 71.0 | 3.8 |

Example 31

A series of samples were made based in part on the results of Examples 17–30. All of these samples comprised 30 parts Oligomer B, 65 parts trifunctional acrylate (SR-499), 0.3 parts wetting agent (FLUORAD FC-431) and 5 parts photoinitiator. As the photoinitiator, the DAROCUR 1173 photoinitiator was used successfully by itself as well as other photoinitators including combinations of benzophenone and DAROCUR 1173 photoinitiator, and benzophenone and IRGACURE 184 photoinitiator. The samples were coated onto a substrate according to Coating Procedure A and cured according to Coating Procedure A. Abrasion Resistance, Scratch Hardness and Strip Time were determined for the cured coatings according to the Test Methods A, B, and C.

Using an initiator system of 5 parts DAROCUR photoinitiator and one additional part of benzophenone the abrasion resistance after a 15 seconds irradiation was up to 82% gloss retention at 20°. The typical scratch hardness of these formulations, when cast onto Sealed PVC Tile (sealed with a poly(vinylidene dichloride) primed polyester film floor sealer commercially available under the trade designation "TECHNIQUE" from S. C. Johnson, Milwaukee, Wis.) was 800–1000 g. When coated over conventional floor finishes, delamination was commonly observed at forces of as little as 200 g. Strip time from Sealed PVC Tile (when sealed with a floor finish available under the trade designation "CORNERSTONE" commercially available from Minnesota Mining and Manufacturing Company) was about 2–3 minutes.

Examples 33–60

Examples 33–60 were prepared and evaluated for abrasion resistance according to Test Method A. All samples contained 0.3 parts wetting agent (FLUORAD FC-431). The formulations of the Examples were coated onto PVC Tile at a dry coating weight of 2.5 g/ft$^2$ (26.9 g/m$^2$) using Coating Method A and cured using Curing Method A. The compositions for Examples 33–60 and the abrasion resistance data is set forth in Table 3. Analysis of the results indicates that formulations with reduced amounts of the SR-335 monofunctional acrylate have the best durability.

TABLE 3

Examples 33–60

| Formulation Example | Parts Oligomer A | Parts SR-454 | Parts SR-335 | Parts DAROCUR 1173 | % 20° Gloss Retention | % 60° Gloss Retention |
| --- | --- | --- | --- | --- | --- | --- |
| 33 | 45.00 | 35.00 | 20.00 | 5 | 62.50 | 67.88 |
| 34 | 30.00 | 20.00 | 50.00 | 5 | No Cure | No Cure |
| 35 | 30.00 | 50.00 | 20.00 | 5 | 62.80 | 37.13 |
| 36 | 35.00 | 25.00 | 40.00 | 5 | No Cure | No Cure |
| 37 | 30.00 | 50.00 | 20.00 | 5 | 29.39 | 36.47 |
| 38 | 30.00 | 20.00 | 50.00 | 5 | No Cure | No Cure |
| 39 | 45.00 | 35.00 | 20.00 | 5 | 48.56 | 56.81 |
| 40 | 35.00 | 40.00 | 25.00 | 5 | 53.81 | 59.69 |
| 41 | 60.00 | 20.00 | 20.00 | 5 | 57.43 | 68.23 |
| 42 | 60.00 | 20.00 | 20.00 | 5 | 46.32 | 57.15 |
| 43 | 30.00 | 35.00 | 35.00 | 5 | No Cure | No Cure |
| 44 | 50.00 | 25.00 | 25.00 | 5 | 65.36 | 76.89 |
| 45 | 45.00 | 20.00 | 35.00 | 5 | No Cure | No Cure |
| 46 | 40.00 | 30.00 | 30.00 | 5 | No Cure | No Cure |
| 47 | 57.50 | 30.00 | 12.50 | 5 | 52.90 | 70.60 |
| 48 | 50.00 | 30.00 | 20.00 | 5 | 56.90 | 64.90 |
| 49 | 50.00 | 50.00 | 0.00 | 5 | 56.80 | 75.20 |
| 50 | 57.50 | 42.50 | 0.00 | 5 | 51.20 | 69.20 |
| 51 | 60.00 | 38.33 | 1.67 | 5 | 59.50 | 77.20 |
| 52 | 50.00 | 30.00 | 20.00 | 5 | 59.60 | 68.80 |
| 53 | 65.00 | 35.00 | 0.00 | 5 | 68.30 | 79.00 |
| 54 | 65.00 | 30.00 | 5.00 | 5 | 62.70 | 75.50 |
| 55 | 50.00 | 50.00 | 0.00 | 5 | 53.40 | 74.40 |
| 56 | 57.50 | 36.25 | 6.25 | 5 | 64.40 | 74.80 |
| 57 | 50.00 | 40.00 | 10.00 | 5 | 60.80 | 70.10 |
| 58 | 50.00 | 40.00 | 10.00 | 5 | 66.30 | 73.50 |
| 59 | 60.00 | 31.67 | 8.33 | 5 | 68.20 | 80.80 |
| 60 | 57.50 | 36.25 | 6.25 | 5 | 74.20 | 80.50 |

Example 32

A series of samples were developed based in part on the results of Example 16. These samples comprised 40 parts Oligomer C; 45 parts trifunctional acrylate (SR-499), 10 parts difunctional acrylate (SR-306), 5 parts photoinitiator and 0.3 parts wetting agent (FLUORAD FC-431). The DAROCUR 1173 photoinitator and other photoinitiators were all used successfully including combinations of benzophenone and DAROCUR 1173 photoinitator, and benzophenone and IRGACURE 184 photoinitator. The samples were coated onto a substrate according to Coating Procedure A and cured according to Coating Procedure A. Abrasion Resistance, Scratch Hardness and Strip Time were determined for the cured coatings according to the Test Methods A, B, and C. The abrasion resistance (% 20° Gloss Retention) was consistently 85%, the scratch hardness was 1300 g, and strip time from Sealed PVC Tile (sealed with a floor sealer commercially available under the trade designation "Cornerstone" from Minnesota Mining and Manufacturing Company) was less than 5 minutes.

Example 61

A series of samples were developed based in part on the results of examples 33–60. These samples comprised 177 parts Oligomer A, 102 parts trifunctional acrylate (SR-454), 21 parts monofunctional acrylate (SR-335), 15 parts photoinitiator (DAROCUR 1173), 0.3 parts wetting agent (FLUORAD FC-431). The formulation were coated over PVC Tile according to Coating Procedure A and cured according to Curing Procedure A. Abrasion resistance, scratch hardness, and strip time data was collected for these samples according to Test Methods A, B, and C. Abrasion resistance showed about 74% gloss retention at 20°. Scratch hardness was greater than 1700 grams. Strip time was about 3 minutes.

Example 62

A coatable composition was prepared comprising 60 parts Oligomer A, 21 parts trifunctional acrylate monomer (SR-454), 12 parts caprolactone acrylate, 2.4 parts photoinitiator (DAROCUR 1173). The sample was coated at about 1 mil thickness onto PVC Tile using coating procedure A and cured for 20 seconds under Curing Procedure B. The resulting coating was tested for strip time according to Test Method C, providing a strip time of about 8 minutes.

Example 63

A coatable composition was prepared comprising 60 parts Oligomer A, 20 parts trifunctional acrylate (SR-454), 20 parts caprolactone acrylate, 5 parts photoinitiator (DAROCUR 1173). The composition was coated on PVC Tile using Coating Procedure A and cured using Curing Procedure A. The resulting coatings were tested according to Test Methods A, B and C. The Abrasion resistance was about 75% gloss retention at 60°, scratch hardness was about 500g. The strip time from PVC Tile was about 3 min.

Examples 64 and 65

Examples 64 and 65 were prepared as set forth in Table 4. Example 65 was identical to Example 64 except that Example 65 was prepared with functionalized silica prepared according to the preparative procedure set forth above. The compositions were coated onto PVC Tile according to Coating Procedure A and cured according to Curing Procedure A to provide a cured coating about 0.25 mm thick. The coatings were tested for abrasion resistance according to Test Method A. The 20° gloss retention values indicated slightly better abrasion resistance for the coating of Example 65 containing the functionalized silica.

Examples 66–71

To determine the effect of visible light on the color of cured coatings made according to the invention, a premix was prepared. The premix comprised 30 parts Oligomer C, 65 parts trifunctional acrylate (SR-499), 5 parts photoinitiator as indicated below, 0.3 parts wetting agent (FLUORAD FC-431). The samples were coated at 2.5 $g^2$ (26.9 $g/m^2$) onto off white PVC Tile and cured using Curing Procedure A except that curing times were 15 seconds. The cured coatings were exposed to 6×15 W Philips F15T8BLB bulbs at a distance of approx. 1 inch (approx. 5 $mW/cm^2$, 350–370 nm). Subsequently, the samples were exposed to 6×15 W Philips 15WTLD/03 bulbs at a distance of approx. 1 inch (wavelength of approx. 420 nm). CIELAB coordinates L*, a* and b* are reported.

The L* indicates whiteness, positive a* coordinates measure redness, positive b* coordinates measure yellowness. DE values measure total color deviation, a DE of less than 1–2 is generally imperceptible to the human eye. Based on the data set forth in Table 5, it is apparent that UV exposure causes yellowing which is reversible upon exposure to blue light.

TABLE 5

Examples 66–71

| Example | Parts Premix | Parts Benzophenone | Parts DAROCUR 1173 | Color coordinates after 15 seconds cure | | | Color coordinates after 45 minutes 350–370 nm light | | | | Color coordinates after 40 min. 420 nm light | | | |
|---|---|---|---|---|---|---|---|---|---|---|---|---|---|---|
| | | | | L* | a* | b* | L* | a* | b* | DE | L* | a* | b* | DE |
| 66 | 9.5 | 0.0 | 0.5 | 87.82 | 1.03 | 4.67 | 86.84 | 1.17 | 8.72 | 4.17 | 86.91 | 1.20 | 5.91 | 1.55 |
| 67 | 9.5 | 0.1 | 0.4 | 88.25 | 1.01 | 4.81 | 86.92 | 1.19 | 8.31 | 3.75 | 87.00 | 1.16 | 5.61 | 1.49 |
| 68 | 9.5 | 0.2 | 0.3 | 88.31 | 1.01 | 4.74 | 87.06 | 1.11 | 7.19 | 2.75 | 86.99 | 1.14 | 5.56 | 1.56 |
| 69 | 9.5 | 0.3 | 0.2 | 88.25 | 1.00 | 4.79 | 87.00 | 1.12 | 7.04 | 2.58 | 86.94 | 1.10 | 5.55 | 1.52 |
| 70 | 9.5 | 0.4 | 0.1 | 87.61 | 1.06 | 5.04 | 86.98 | 1.19 | 7.83 | 2.86 | 87.06 | 1.11 | 5.66 | 0.83 |
| 71 | 9.5 | 0.5 | 0.0 | 87.60 | 1.04 | 4.91 | 86.93 | 1.18 | 7.81 | 2.98 | 87.00 | 1.09 | 5.67 | 0.97 |

TABLE 4

Example 64 and 65

| Example | Composition | Average % 20° Gloss Retention | Standard Deviation |
|---|---|---|---|
| 64 | 40 parts Oligomer C, 45 parts trifunctional acrylate (SR-499), 10 parts difunctional acrylate (SR-306), 3 parts benzophenone, 2 parts DAROCUR 1173 photoinitiator | 83.9 | 4.5 |
| 65 | 40 parts Oligomer C, 45 parts trifunctional acrylate (SR-499) containing 10% functionalized silica, 10 parts difunctional acrylate (SR-306), 3 parts benzophenone, 2 parts DAROCUR 1173 photoinitiator | 87.9 | 2.1 |

Examples 72–80

An oligomer was prepared as in the Preparation of Oligomer B by combining 42 parts allophanated HDI trimer (DESMODUR XP-7100), 2-hydroxyethyl acrylate, and 2-dimethylamino-ethanol (equivalent ratio of 3:2:1). The oligomer was combined with 48 parts trifunctional acrylate (SR-499), 5 parts difunctional acrylate (SR-306), 3 parts benzophenone, 2 parts DAROCUR 4265 photoinitiator and 0.3 parts wetting agent (FLUORAD FC-171) to provide a UV curable coatable composition. For some of the Examples, EBECRYL 350 acrylated silicone was added to the coatable composition as a release material.

The coatable compositions were tested for adhesion to both PVC Tile and to Sealed PVC Tile. Sealed PVC Tile was prepared by treating with a primer or sealer applied by hand with gauze to provide a smooth even coating. The primer was then allowed to dry in air at ambient temperature and humidity.

Coatable composition was then applied to both Sealed PVC Tile and PVC Tile according to Coating Procedure A and then UV cured according to Curing Procedure A using a 10 second exposure time. After the curing step, cuts were made with a razor blade through the cured coating and the primer (when present) and into the tile substrate to form a grid of 1/8"×1/8" (0.32 cm×0.32 cm) squares. Tape ("SCOTCH Rug and Carpet Tape" available from Minnesota Mining and Manufacturing Company) was applied onto the square pattern with a 2.3 kg roller. The tape was then peeled by hand from the tile by grabbing an end thereof and pulling the tape back over itself at about a 180° angle. Adhesion was determined by visual inspection of both the tile and the removed tape to determine the percentage of the square sections removed from the tile. A value of 0% adhesion means all of the coating was removed from the tile while 100% adhesion means none of the coating was removed. In general, all UV cured coatings adhered well to the tile substrate with better adhesion observed on Sealed PVC Tile, especially those sealed with the ROSHIELD 3120 latex.

The composition of the UV curable coatings, the primer layer used and the data for the adhesion test are all summarized in Table 6. Unless otherwise indicated, the coatings for these Examples comprised 100 parts of the coatable composition without added acrylated silicone.

TABLE 6

(Examples 72–80)

| EXAMPLE | Primer | % Adhesion |
|---|---|---|
| 72 | none | 0 |
| 73 (100 parts coating + 1 part EBECRYL 350 acrylated silicone) | none | 0 |
| 74 | TECHNIQUE | 10 |
| 75 | TOPLINE | 0 |
| 76 | ROSHIELD 3120 | 100 |
| 77 | TOPLINE overcoated with ROSHIELD 3120 | 90 |
| 78 (100 parts coating + 1 part EBECRYL 350 acrylated silicone) | ROSHIELD 3120 | 100 |
| 79 (100 parts coating + 2 parts EBECRYL 350 acrylated silicone) | ROSHIELD 3120 | 100 |
| 80 (100 parts coating + 3 part EBECRYL 350 acrylated silicone) | ROSHIELD 3120 | 100 |

Although preferred embodiments of the invention have been described in detail, it will be understood that changes and modifications to the described embodiments may be made by those skilled in the art without departing from the true spirit and the scope of the invention, as set forth in the following claims.

We claim:

1. A method for applying a protective coating to a substrate, comprising:

(a) applying a coatable acrylated latex primer composition to the substrate;

(b) drying the primer composition to form an acrylated polymer primer coat over the substrate;

(c) applying a radiation curable coatable composition to the primer coat before curing the primer coat; and (d) hardening the radiation curable coatable composition by exposing the composition to ultraviolet radiation to form a protective coating over the substrate.

2. The method of claim 1, wherein the substrate comprises a floor.

3. The method of claim 2, wherein the floor comprises vinyl tile.

4. The method of claim 1, wherein the radiation curable coatable composition comprises an isocyanurate monomer.

5. The method of claim 1, wherein the radiation curable coatable composition comprises a polymerizable monomer selected from the group consisting of an acrylated monomer, an N-vinyl monomer, a vinyl ether, and a styrenic monomer.

6. The method of claim 5, wherein the polymerizable monomer is an acrylated monomer.

7. The method of claim 1, wherein the radiation curable coatable composition further comprises a photoinitiator.

8. A stripper for a cured coating comprising water, benzyl alcohol, n-octylamine, glycolic acid, and a surfactant.

9. The stripper of claim 8, further comprising a dye.

10. The stripper of claim 8, further comprising a thickening agent.

11. The stripper of claim 8, further comprising a fragrance.

12. The stripper of claim 8, wherein the stripper has a neutral pH.

13. A method of stripping a cured coating on a substrate comprising:

(a) applying the a stripper composition of claim 8 to the cured coating;

(b) waiting for a period of time sufficient to loosen the cured coating; and (c) removing the cured coating.

14. The method of claim 13, wherein the cured coating is a cured acrylate coating.

15. A primer composition comprising an acrylated latex, water, a leveling aid comprising an ammonium salt of a styrene maleic anhydride copolymer, and a surfactant.

16. The primer of claim 15, wherein the primer has a solids content between about 2 and about 40% by weight.

17. The primer of claim 16, wherein the primer has a solids content between about 2 and about 20% by weight.

18. The primer of claim 17, wherein the primer has a solids content between about 4 and about 15% by weight.

* * * * *

UNITED STATES PATENT AND TRADEMARK OFFICE
CERTIFICATE OF CORRECTION

PATENT NO. : 6,780,472 B2
DATED : August 24, 2004
INVENTOR(S) : Hamrock, Steven J.

It is certified that error appears in the above-identified patent and that said Letters Patent is hereby corrected as shown below:

Column 4,
Line 2, delete "cylcoalkanediyl" and insert -- cycloalkanediyl --, therefor.

Column 8,
Line 60, delete "cross-linked" and insert -- crosslinked --, therefor.

Column 9,
Line 44, delete "a-methylstyrene" and insert -- α- methylstyrene --, therefor.

Column 11,
Line 30, after "additives" delete ";" and insert -- , --, therefor.

Column 13,
Line 23, after "to" delete ".".

Column 14,
Line 5, after "foregoing" delete ",".

Column 15,
Line 50, after "materials" insert -- used and --.

Column 21,
Line 52, after "C" delete ";" and insert -- , --, therefor.

Column 24,
Line 11, delete "2.5 g$^2$" and insert -- 2.5 g/ft$^2$ --, therefor.

Signed and Sealed this

Thirtieth Day of November, 2004

JON W. DUDAS
*Director of the United States Patent and Trademark Office*